(12) United States Patent
Lopez et al.

(10) Patent No.: US 6,685,841 B2
(45) Date of Patent: Feb. 3, 2004

(54) NANOSTRUCTURED DEVICES FOR SEPARATION AND ANALYSIS

(76) Inventors: Gabriel P. Lopez, 1105 Dartmouth NE., Albuquerque, NM (US) 87106; Steven R. J. Brueck, 5601 Cometa Ct. NE., Albuquerque, NM (US) 87111; Linnea K. Ista, 4912 Inspiration Dr., SE., Albuquerque, NM (US) 87108; Michael O'Brien, 320 Harvard Dr., SE. #87, Albuquerque, NM (US) 87106; Stephen D Hersee, 3712 Silver Ave. SE., Albuquerque, NM (US) 87108

( * ) Notice: Subject to any disclaimer, the term of this patent is extended or adjusted under 35 U.S.C. 154(b) by 1 day.

(21) Appl. No.: 10/073,935

(22) Filed: Feb. 14, 2002

(65) Prior Publication Data

US 2002/0125192 A1 Sep. 12, 2002

Related U.S. Application Data

(60) Provisional application No. 60/268,365, filed on Feb. 14, 2001.

(51) Int. Cl.[7] .......................... B01D 57/00; B01D 15/08; H01L 21/00; C12Q 1/00
(52) U.S. Cl. .................... 210/767; 210/198.2; 210/635; 210/656; 204/600; 436/161; 436/180; 435/4; 428/304.4; 428/310.5; 438/1; 438/800; 216/2; 216/56; 137/833
(58) Field of Search ............................... 210/243, 198.2, 210/511, 321.84, 500.22, 500.26, 634, 635, 638, 639, 650, 651, 656, 806; 435/4, 6, 7.1, 287.1, 287.3; 422/70, 99, 101, 104; 436/161, 178, 188; 216/2, 56; 204/450, 456, 600–605

(56) References Cited

U.S. PATENT DOCUMENTS

| | | |
|---|---|---|
| 3,855,133 A | 12/1974 | Roehsler |
| 4,801,380 A | 1/1989 | Parker et al. |
| 4,814,082 A | 3/1989 | Wrasidlo |
| 4,814,088 A | 3/1989 | Kutowy et al. |
| 4,902,424 A | 2/1990 | Wrasidlo |
| 4,935,141 A | 6/1990 | Buck et al. |
| 4,969,998 A | 11/1990 | Henn |
| 5,013,337 A | 5/1991 | Bedard et al. |
| 5,019,263 A | 5/1991 | Haag et al. |
| 5,130,025 A | 7/1992 | Lefebvre et al. |
| 5,145,584 A | 9/1992 | Swamikannu |
| 5,266,207 A | 11/1993 | Boye et al. |
| 5,474,675 A | 12/1995 | Kupka |
| 5,716,527 A | 2/1998 | Deckman et al. |
| 5,753,014 A | 5/1998 | Van Rijn |
| 5,798,042 A | 8/1998 | Chu et al. |
| 5,876,830 A | 3/1999 | Michl et al. |
| 5,938,923 A | 8/1999 | Tu et al. |
| 5,993,661 A | 11/1999 | Ruckenstein et al. |
| 6,043,177 A | 3/2000 | Falconer et al. |

(List continued on next page.)

OTHER PUBLICATIONS

PGPUBS Document US2003/03528, published Jun. 19, 2003, filed Dec. 9, 2002 having an effective filing date Sep. 17, 1999, Moya et al.*

Primary Examiner—Joseph Drodge
(74) Attorney, Agent, or Firm—Jagtiani & Guttag

(57) ABSTRACT

The present invention provides a matrix comprising an array of nanostructures that exhibit a variation (gradient) in physical properties (such as size or pitch) in at least one direction of the plane containing said array. A method for forming an array having a gradient property is also provided. In addition, a separation method is provided comprising the steps of: providing a matrix comprising an array of nanostructures arranged so that the array has the property of a gradient; and conducting at least one biomolecule separation process to separate biomolecules in a composition containing a plurality of biomolecules using the matrix.

34 Claims, 11 Drawing Sheets

U.S. PATENT DOCUMENTS

| | | |
|---|---|---|
| 6,044,981 A | 4/2000 | Chu et al. |
| 6,051,517 A | 4/2000 | Funke et al. |
| 6,060,415 A | 5/2000 | Chao et al. |
| 6,090,289 A | 7/2000 | Verduijn et al. |
| 6,100,393 A | 8/2000 | Lopez Ortiz et al. |
| 6,113,794 A | 9/2000 | Kumar et al. |
| 6,113,795 A | 9/2000 | Subramaniam et al. |
| 6,177,373 B1 | 1/2001 | Sterte et al. |
| 6,190,638 B1 | 2/2001 | Anthonis et al. |
| 6,243,348 B1 * | 6/2001 | Goodberlet |
| 6,264,044 B1 | 7/2001 | Meyering et al. |
| 6,296,752 B1 * | 10/2001 | McBride et al. ............ 204/600 |
| 6,361,671 B1 * | 3/2002 | Mathies et al. ............ 210/656 |
| 6,368,871 B1 * | 4/2002 | Christel et al. ............ 436/180 |

* cited by examiner

Fig. 5A
Fig. 5B
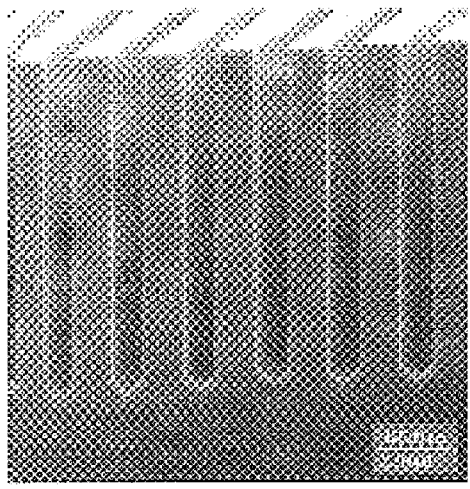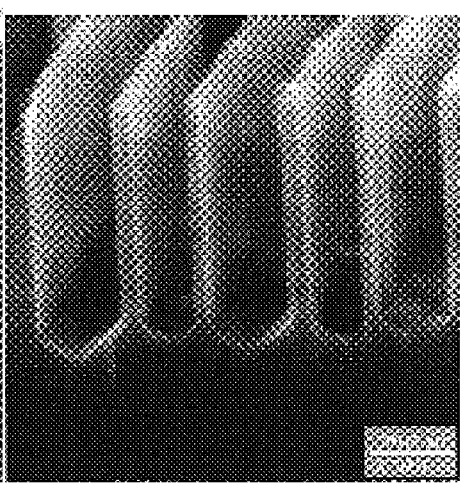

NANOSTRUCTURED DEVICES FOR SEPARATION AND ANALYSIS

CROSS-REFERENCE TO RELATED APPLICATIONS

This application makes reference to U.S. Provisional Patent Application No. 60/268,365, entitled "Nanostructured Devices for Separation and Analysis," filed on Feb. 14, 2001, the entire contents and disclosure of which is hereby incorporated by reference.

GOVERNMENT INTEREST STATEMENT

This invention is made with government support under grant number DAAD19-99-1-0196 awarded by the United States Army Research Office. The government may have certain rights in this invention.

BACKGROUND OF THE INVENTION

1. Field of the Invention

The present invention relates generally to nanostructured matrices, and more particularly to the fabrication and use of nanostructured matrices for separation and analysis of molecules.

2. Description of the Prior Art

Polyacrylamide gel electrophoresis (PAGE) remains the standard for protein separation and identification in biotechnology. Nevertheless, the set of separation strategies that rely on this technique are hampered by: (1) inconvenience of preparation of the variety of gels needed for the separations, (2) inherent inconsistencies in production conditions; and therefore, irreproducibility between different batches of gels, (3) limited resolution and dynamic range of biomolecular separations, (4) susceptibility of the polymer to degradation under high electric fields, (5) lack of reusability, and (6) difficulty in incorporation of these techniques into strategies for development of multi-dimensional (multi-technique) integrated separation systems.

Gradient PAGE techniques are recognized to have the potential to have excellent resolution and dynamic range, but their utility is greatly hampered by the need for cumbersome gel preparation protocols and lack of reproducibility.

The demand for precise separation of molecules using small sample volumes is increasing. Separation of molecules across matrices or membranes has been known for long in the art. Separations are generally achieved by employing barriers that allow cut-offs at a precise molecular weight or by size-exclusion. The art describes structures where molecular transport and filtration take place perpendicular to the surface of the separating material. The currently available systems, however, suffer from a number of drawbacks. For example, biomolecules may not be amenable to separation by many of the available systems. For example, reaction steps may denature or inactivate the molecules themselves. The matrices formed are generally composed of non-uniform structures. Even where a gradation in size of structures is required, they may be random or at best have to be serially and sequentially arrayed through a cumbersome process of lithography. Fabrication of such separation devices also pose problems in terms of batch-to-batch variations and consequently poor reproducibility of results therefrom. Lack of efficiency of separation or loss of sample volume are also encountered.

Nano-filtration of molecules using "Brownian ratchets" in which assymetric diffusion leads to separation of molecules based on their size (van Oudenaarden et al. Science, 285: 1046–1052, 1999) has been tried with some success. Chou et al., Proc. Natl. Acad. Sci. 96, 13762–13765, 1999, attempted separation of DNA molecules using microsystems formed by conventional photolithography. However, the developments have not gained ground with users primarily because of the difficulty of preparation of the nanofluidic systems and the associated high-cost of fabrication. Other separation matrices such as gradient polyacrylamide gels, where one-dimension filtration was achieved by manipulating pore-size through control of cross-linker, monomer and solvent concentrations, has shown limited success. Even though the separation is effective, the preparation process is tedious and the results obtained are not reproducible. "Artificial gels" incorporating regular arrays of nanoscale pillars created through electron beam and/or imprint lithography have been described, for example, in U.S. Pat. No. 6,110,339 to Brueck et al. and by Turner et al. (J. Vac. Sci. Technol. B., 16 3835–3840, 1998). All these nanolithographically-defined structures utilize regular arrays of uniform-sized nanostructures throughout the separation matrix. Thus, the systems suffer from resolution and flexibility limitations. It is also difficult to integrate such a system with other more complex separation devices. Thus, the need for an efficient, highly-resolving, flexible, cost-efficient and reproducible molecular-separation matrix, is largely unmet.

SUMMARY OF THE INVENTION

It is therefore an object of the present invention to provide a highly-efficient and facile nanostructured matrix for separation and analysis of molecules.

It is a further object of the present invention to provide a matrix that enables gradient or non-uniform transport of molecules across a plane parallel to the surface of the matrix.

A further object of the present invention is to enable integration of multi-dimensional multi-technique molecular separation systems into a single platform.

Yet another object of the present invention is to provide for customized fabrication of a nanostructured separation matrix including an array having a gradient property.

It is yet another object of the present invention is to provide a nanostructured matrix that may be easily cast to cater to different ranges of molecular separations, in terms of resolution and dynamics.

Another object of the present invention is to enable uniform consistency in the composition of the nanostructures forming the separation matrix.

Yet another object of the present invention is to enable separation and/or identification of a molecular species.

A further object of the present invention is to enable calibration-free use of the separation/analysis process.

Yet another object of the present invention is to enable multiple use of a single separation matrix.

A further object of the present invention is to enable parallel production of separation matrices at relatively low cost.

In all of the above embodiments, it is an object to provide enhanced reproducibility and resolution in the separation of molecules.

According to a first broad aspect of the present invention, there is provided a matrix comprising an array of nanostructures arranged so that the array has a gradient property.

According to second broad aspect of the invention, there is provided a method for forming an array having a gradient property comprising the steps of: (a) providing a substrate;

and (b) forming nanostructures on the substrate to form an array having a gradient property.

According to a third broad aspect of the invention, there is provided a separation method comprising the steps of: (a) providing a matrix comprising an array having a gradient property, the array comprising nanostructures; and (b) conducting at least one biomolecule separation process to separate biomolecules in a composition containing a plurality of biomolecules using the matrix.

Other objects and features of the present invention will be apparent from the following detailed description of the preferred embodiment.

BRIEF DESCRIPTION OF THE DRAWINGS

The invention will be described in conjunction with the accompanying drawings, in which:

FIGS. 5A and 5B are micrographs showing transfer of interferometric lithography patterns into deep structures in Si using KOH anisotropic etching, with FIG. 5A showing the original period of 360 nm with about 1 micrometer deep etched grooves and FIG. 5B showing the 180 nm period, frequency-doubled structure corresponding to the lithographic result of FIG. 4;

DETAILED DESCRIPTION OF THE PREFERRED EMBODIMENT

Definitions

Figure 1:
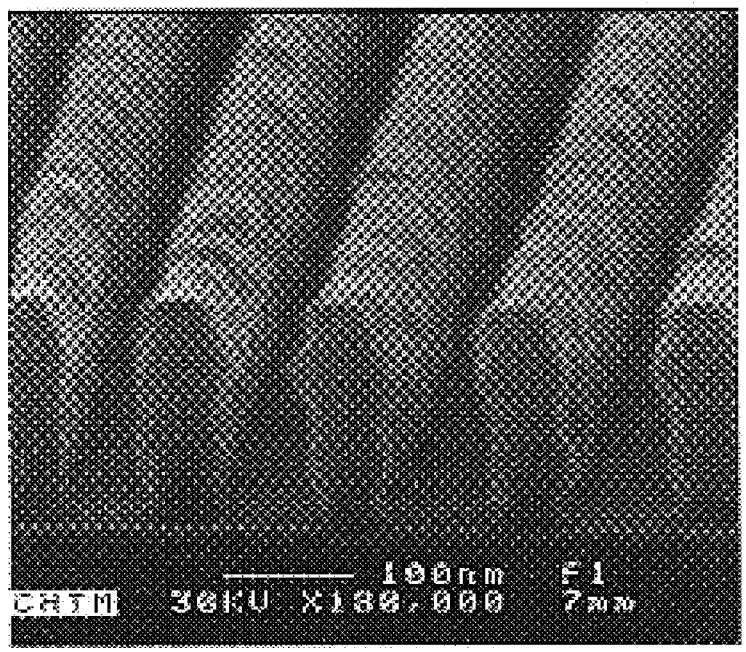
FIG. 1 is a micrograph showing a 150-nm period photoresist grating written with 213 nm light.

For the purposes of the present invention, the term "nanostructure" refers to a protrusion or void having a diameter in at least one direction of 1 to 500 nm.

For the purposes of the present invention, the term "diameter" refers to the distance across a nanostructure through the middle and perpendicular to the axis of the nanostructure, parallel to the plane of the substrate (upon which the nanostructure is located).

For the purposes of the present invention, the term "axis" refers to a line running along the middle of a nanostructure in the direction the nanostructure's longest dimension parallel to the surface of the substrate on which the nanostructure is located.

For the purposes of the present invention, the term "protrusion" refers to a structure that protrudes from the surface of a substrate or that protrudes from a portion of a substrate that has been etched. The protrusions of the present invention may be any convenient size or shape. The cross-section of a protrusion may be circular, square, rectangular, oval, elliptical, etc.

For the purposes of the present invention, the term "channel" refers to a gap between any two protrusions. The channels of the present invention may be any convenient size or shape.

For the purposes of the present invention, the term "array" refers to an arrangement of nanostructures.

For the purposes of the present invention, the term "gradient" refers to an array where channels, protrusions or other features at one end of the array are larger than those at an opposite end of the array.

For the purposes of the present invention, the term "continuous gradient" refers to a gradient where successive rows of channels, protrusions or other features decrease in size substantially continuously from one end of the gradient to the other end of the gradient.

For the purposes of the present invention, the term "non-continuous gradient" refers to a gradient that includes regions of the gradient having successive rows of channels, protrusions or other features that are substantially the same size.

For the purposes of the present invention, the term "matrix" refers to a substrate having an array of nanostructures present on or in at least a portion of the substrate. A matrix of the present invention preferably has at least one gradient on or in the substrate formed by the nanostructures. Examples of a matrix of the present invention include one or more arrays located on a chip, such as a semiconductor chip, biochip, etc. Methods for making biochips which may be readily adapted for use in making biochips of the present invention are described in U.S. Pat. No. 6,174,683, the entire contents and disclosure of which is hereby incorporated by reference.

For the purposes of the present invention, the term "interferometric lithography" (IL) refers to a process of lithography that involves interference patterns of two (or more) mutually coherent light waves. The angles between the light propagation vectors of the waves are sufficiently large to produce an interference pattern that has a high spatial frequency. The resulting interference pattern may have nanoscale dimensions. Examples of interferometric lithography techniques that may be used in the present invention are described in Chen XL, Brueck SRJ, "Imaging interferometric lithography: approaching the limits of optics" in *Optics Letters*, 24, pp. 124–126 (1999), in "Imaging interferometric lithography: A wavelength division multiplex approach to extending optical lithography, Chen XL, Brueck SRJ, *Journal of Vacuum Science and Technology B*, vol. 16, pp. 3392–3397 (1998), in U.S. Pat. No. 5,759,744 to Brueck et al., in U.S. Pat. No. 6,233,044 to Brueck et al., and U.S. Pat. No. 6,042,998 to Brueck et al, the entire contents and disclosures of which are hereby incorporated by reference.

For the purposes of the present invention, the term "biomolecules" refers to biologically derived macromolecules such as peptides, small polypeptidess, long polypeptides, proteins, antigens, antibodies, tagged proteins, oligonucleotides, nucleotides, polynucleotides, aptamers, DNA, RNA, carbohydrates, etc. and complexes thereof.

For the purposes of the present invention, the term "size exclusion separation process" refers to separating particles, such as biomolecules, by size based on the ability of smaller particles to pass through smaller openings or channels than larger particles.

For the purposes of the present invention, the term "gel electrophoretic mobility separation process" refers to any conventional electrophoresis separation technique such as two-dimensional polyacrylamide gel electrophoresis. Polyacrylamide gel electrophoresis (PAGE) is used to separate biomolecules, usually proteins or DNA fragments, by the ratio of each biomolecule's mass to charge. Proteins may be separated in either their native state, or denatured by the addition of a detergent such as SDS (Sodium Dodecyl Sulfate). Further resolution may be obtained in some cases by making a gel with a gradient either in the concentration of the acrylamide or in the degree of crosslinking within the gel matrix. The array of the present invention may be used to doing equivalent molecular weight separations, with either electrical currents or flow as the drive force.

For the purposes of the present invention, the term "isoelectric focusing separation process" refers to the separation of charged biomolecules, such as proteins and peptides, by the each biomolecule's isoelectric point. A pH gradient is generally generated using a mixture of ampholytes within the separation matrix, usually polycrylamide. The biomolecules in the mixture then migrate to the region where the pH is equal to a particular biomolecule's isoelectric point, at which time the charged biomolecule become electrically neutral. This technique, combined with subsequent separation by SDS-PAGE, is used in traditional two-dimensional gel electrophoresis. Similar pH gradients may be generated using an array of the present invention including a two-dimensional gradient, using traditional isolectric focusing with soluble ampholytes or by using chemical patterning techniques, or immobilization of ampholytes after electrical focusing. Examples of capillary-based isoelectric focusing separation processes suitable for use with the present invention are described in Thorman, Tsai, Michaud, Mosher and Bier "Capillary Isoelectric-Focusing: Effects of Capillary, Geometry, Voltage Gradient and Addition of Linear Polymer" *J. Chromatography*, 398:75–86 (1987), the entire contents and disclosure of which are hereby incorporated by reference.

For the purposes of the present invention, the term "asymmetric diffusion separation process" refers to a separation process in which steric constraints drive diffusion preferentially in one direction. Examples of asymmetric diffusion separation processes suitable for use with the present invention are described in Van Oudenaarden et al., *Science*, 285: 1046–1052 (1999), the entire contents and disclosure of which are hereby incorporated by reference.

For the purposes of the present invention, the term "entropic trapping separation process" refers to separations using nanostructured devices of alternating thin and thick regions, with the thin regions being smaller than the radius of gyration of the biomolecule being separated. Under an electrical field, the molecules repeatedly change conformation, costing entropic free energy, thus limiting mobility. An example of an entropic trapping separation process suitable for use with the present invention is described in Han J, Craighead HD, "Separation of long DNA molecules in a microfabricated entropic trap array" *Science*, 288:1026–1029 (2000), the entire contents and disclosure of which is hereby incorporated by reference.

For the purposes of the present invention, the term "hydrophobic interaction chromatography separation process" refers to a technique whereby molecules are partitioned between a hydrophobic matrix and a hydrophilic solvent. The degree of hydrophobicity of the target molecule determines the target molecule's retention time. The array of the present invention may be modified to incorporate a gradient of hydrophobicities or to create a milieu in which the hydrophobicity may be rapidly and reversibly changed, thus providing a driving force for molecular movement.

For the purposes of the present invention, the term "affinity chromatography separation process" refers to a chromatography process that takes advantage of specific chemical interactions between a target molecule and a chromatographic matrix. One of the most widely used forms of affinity chromatography employs immunoaffinity in which an antibody or series of antibodies are immobilized on a support. Other affinity agents include enzymes that interact with specific targets or receptors. Another example of affinity chromatography is a molecular recognition separation process such as the separation of long DNA molecules in a microfabricated entropic trap array. An array of the present invention may be used for both the generation of affinity matrices and for the subsequent use of affinity matrices.

For the purposes of the present invention, the term "enantiomeric resolution separation process" refers to a process to separate organic particles, such as biomolecules by chirality. Enantiomeric resolution is especially important in carbohydrate separations where differences between different glycosides are exclusively enantiomeric. Indeed, common chiral selectors are cyclodextrins used in capillary electrophoresis. Macrocyclic antibiotics and crown ethers are commonly used selectors. Selectors may be used either be used either globally or in zones of the array of the present invention to confer yet another means of separation.

For the purposes of the present invention, the term "capillary electrophoresis separation process" refers to a separation process in which separation takes place in a liquid rather in a gel matrix. Capillary electrophoresis allows for separations to be done on smaller quantities of material and with improved resolution in comparison to convention gel electrophoresis processes. The channels in an array of the present invention may be arranged to generate a capillary type arrangement in a second direction following separations based on chemical properties (e.g., IEF, affinity, hydrophobic interaction chromatography or enantiomeric separation) or capillaries may be applied as a third dimension.

For the purposes of the present invention, the phrase "comprises Si" refers to silicon and any silicon complex, compound, etc. that includes silicon, such as $SiO_2$, glass, etc.

Description

The present invention provides, in part, for robust, inexpensive and reproducible methods for forming separation matrices for gradient separations based on, for example, electrophoresis and size exclusion that will have all the positive traits of gradient PAGE. These matrices may be adapted for a host of variant separation strategies, including electrophoresis, detergent solubilization, native electrophoresis, isoelectric focusing, 2D-electrophoresis, hydrophobic interaction, and affinity chromatography. The methods of fabrication discussed herein may also be adapted by existing microfabrication and integration facilities.

The present invention provides for separation of molecular species across a nanostructured matrix, a method of fabricating nanostructures comprising the matrix and the use of such a matrix for separation and/or analysis of molecules by defining the physical size and/or chemical features of the nanostructures as a means of screening. The present invention may be used to separate biological materials, such as proteins, carbohydrates, and nucleic acids as well as non-biological materials, such as synthetic polymers. These nanostructures may be made out of a variety of materials, including silicon, thus providing systems that may be easily chemically modified for additional flexibility. The use of lithography to generate nanostructured separation matrices has advantages over other techniques (such as traditional acrylamide gel polymerization) since it (1) creates highly ordered structures, (2) gives the possibility of creating macroscopic arrays of continually varying size or chemistry across one dimension, (3) is highly reproducible, and (4) may be easily implemented in the creation of complex, integrated separation systems that are disposable or reusable. Furthermore, the use of lithographically defined separation matrices lends itself to the facile implementation of these matrices into multi-level, 3-dimensional separation devices in which different screening mechanisms allow enhanced separations. The present invention aims to eliminate some of the current limitations by the fabrication of highly uniform and reproducible nanostructured separation systems prepared by nano- and microlithography.

Nanolithographically-defined Gradients:

Using an advanced lithographic technique such as interferometric lithography (IL) capable of producing nanostructures, patterns of nanostructures may be rapidly created over wide, macroscopic areas at low cost (compared to other techniques such as electron beam lithography). In addition, it may be used to easily generate arrays of nanostructures (protrusions or channels) whose dimensions vary semi-continuously in the plane of surface of the material being patterned. IL has advantages over other methods that might be used to construct nanopatterned fluidic structures (e.g., electron beam lithography, X-ray lithography, or local probe lithography) due to the low cost of implementation and the parallel nature of the lithographic technique. Combining IL with conventional lithography allows for the formation of device structures in individual areas and adding a periodic features such as electronic and fluidic connections. Imaging interferometric lithography extends optics to fundamental, deep-subwavelength scales.

Figure 2:
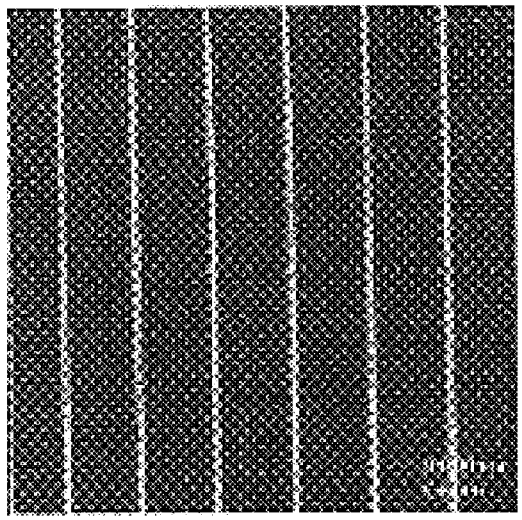
FIG. 2 is a micrograph showing 30-nm photoresist lines.

It is worthwhile at this point to consider the fundamental limits of optical lithography. For the interference of two plane waves in air, the period is given by $\lambda/(2 \sin \theta)$ where $\lambda$ is the optical wavelength and $\theta$ is the angle of incidence. For a 213-nm laser source (fifth harmonic of YAG) this gives a period of ~150 nm (for $\theta=80°$). FIG. 1 shows an example of a large-area, 150 nm period, photoresist grating. It is important to realize that this limit is on the period, not on the feature dimensions. Nonlinearities in the exposure/develop processes and in subsequent processing may reduce the feature to dimensions well below $\lambda/4$. An example in FIG. 2 shows 30-nm developed resist lines on a 360-nm pitch written at a wavelength of 364 nm. The ultimate limit in linewidth is set by material properties and by uniformity of the processing; linewidths as small as 10 nm are routinely achieved. The use of immersion techniques, may further reduce the period by a factor of the refractive index, approximately a factor of 1.5, to a period of ~75 nm. Initial results reproduced the 150 nm pitch of FIG. 1 at a lower angle of incidence.

Figure 3:
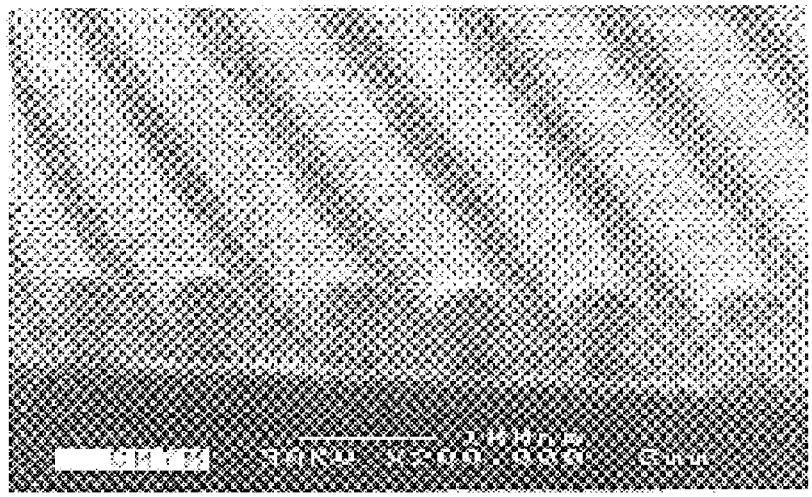
FIG. 3 is a micrograph showing a 108-nm pitch photoresist grating, written using 213 nm light, and immersion in DI water.

Water and higher-index liquids, including liquid Ar (n~1.6) may be used to further extend these results into the sub-100-nm period regime that will be important for biological separations. FIG. 3 shows an initial example of immersion interferometric lithography where the grating period has been reduced to 108 nm with exposure by 213 nm light using immersion in deionized water.

Figure 4:
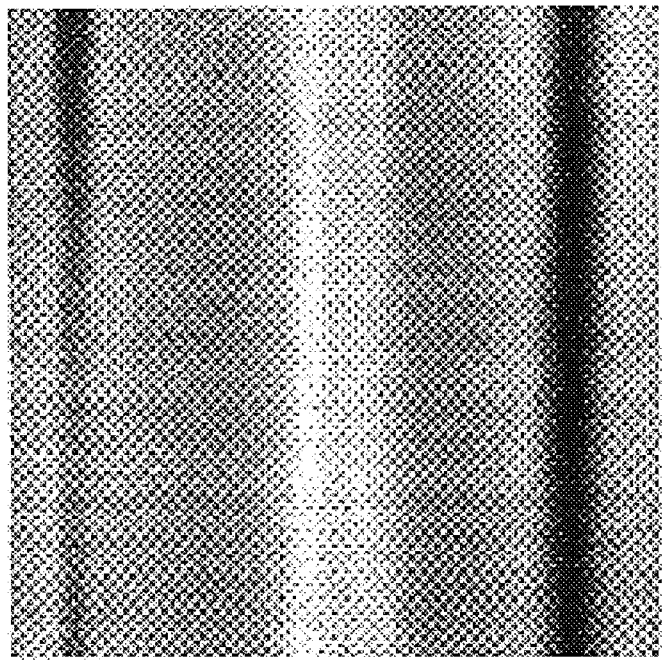
FIG. 4 is a micrograph showing a photoresist line interpolated between two lines etched 360 nm apart into a nitride film demonstrating spatial period division to exent the spatial frequency coverage of optical lithography.

Nonlinear processes may be used to further reduce the period. FIG. 4 shows an example of a photoresist line interpolated between two parallel lines that have already been transferred into a nitride layer. FIG. 5B shows the result of transferring both of these patterns into Si using a KOH etch process. The final period is ~half of the initial IL period. Extending the calculation above with this spatial period division gives a period of ~37 nm and a dense linewidth of ~17 nm ($\lambda/12$).

Importantly, all of these results are macroscopic in scale, e.g., covering areas of ~1 $cm^2$ or larger. A strength of optics is the parallel nature of the exposure, which may be cm's or larger in extent. For a square lattice with a 100-nm pitch and a 1 cm field, there are $10^{10}$ features, well beyond the realistic capabilities of serial techniques such as e-beam and scanning probes. In particular embodiments of the present invention, IL may be extended deep into the nanometer regime (either to feature sizes of ~10 nm or nearest-neighbor distances (aperture sizes) of <10 nm, but not both simultaneously).

A continuously varying channel spacing between nanostructures is desired for many of the bio-separation applications such as various nanofluidic configurations discussed herein.

One approach to a graded structure is to macroscopically vary the intensity across the plane of exposure while keeping the other interference conditions, such as the angles between the light propagation vectors and the polarization, unchanged. One such variation of intensity would be a smooth gradient in intensity of one of the two interfering light waves. This results in interference fringes with uniform spacing but different intensities. The difference in intensity of the fringes leads to differences in exposure of the photoresist used. Because the fringe spacing is not changed, the pitch is uniform. The interference pattern would have even better contrast if both light waves had the same gradient in intensities.

When a positive photoresist is used, the areas corresponding to fringes with stronger intensities leave wider cavities in the photoresist after exposure and developing. The areas corresponding to fringes with weaker intensities leave narrower cavities in the photoresist. When the substrate is etched, these differing widths translate into features in the substrate that have differing widths. The features have the same pitch, however, because the fringe spacing is not altered. This leads to a constant pitch, but a varying line:space ratio. This procedure provides a continuously decreasing channel width that may be accurately controlled over very long distances. Such gradient separation matrices exhibit the favorable traits of gradient gels (high resolution in separation), without the difficulty and irreproducibility associated with their preparation.

Similarly, this technique when used with negative photoresist leaves wider features in the areas corresponding to fringes with weaker intensity and narrower features in the area corresponding to fringes with stronger intensity.

An alternative approach may produce features with a gradient in width and pitch. This may be easily achieved with IL by using a cylindrical lens in one of the beams, while keeping the other beam as a plane wave. In this case the plane of exposure becomes a chord for a number of circular wavefronts. Because the wavefronts have different radii of curvature (spacing of an optical wavelength), the spacing between the interference fringes, as well as the width of the interference fringes, vary along the length of the plane containing the interference fringes on the surface of the photoresist coating the substrate. Similarly, curved surfaces (sections of Newton's rings) may be formed by interfering a plane wave and a spherical wave or two spherical waves of differing radii of curvature.

Other types of separation systems may involve discontinuous gradients. One such system may have differing aperture sizes that may be produced by separate exposures with different intensities, at different pitches through shadow masks, or by using multiple exposure techniques to eliminate rows and/or columns of pillars in certain areas of a previously exposed uniform nano-structured surface.

Variations in size may also be produced chemically. For example, increasing the oxidation of silicon in certain areas of a chip will result in a swelling of the features, reducing the width of some channels while conserving the pitch of the features. Similarly, macroscopic areas may be selectively functionalized with monolayers, reducing the width of channels contained in that area.

One may also electrochemically produce silicon carbide on a silicon substrate. Silicon carbide is suitable for sublimation growth, allowing one to control the width of the modified channels in a certain area. Of course, silicon carbide is only one example of surface modifications that can be performed.

One may also selectively heat a substrate, bringing it close to its annealing temperature. At this time the substrate may be placed under a highly controlled stress. The subsequent strain alters the size of channels. A gradient in temperature across the substrate results in a gradient of strain, and therefore a gradient in channel widths. This technique would only be suitable for substrates without a crystalline structure (such as glass or amorphous silicon, for example).

The very high aspect ratios of FIGS. 5A and 5B were achieved using highly anisotropic wet chemical etching of crystalline Si in KOH, which exhibits a >400:1 etch-rate selectivity for etching the <100> plane relative to the <111> plane of Si. Thus, the vertical sidewalls are nearly perfect <111> Si facets. These structures may be further modified by oxidation. This provides insulation between the Si and the surrounding material (allowing electrophoretic fluidic manipulation) and varies the surface interactions between the nanostructure and the surrounding materials for fluidic applications. Very high aspect ratio, crystal-structure-independent etching processes have been developed to address the need for 3D structures in MEMs technology. These involve pulsed gas processes in which an isotropic etch process is alternated with a surface passivation step to reduce the sidewall etch rate and only etch feature bottoms exposed by ion bombardment. To date, these processes have largely been investigated on micrometer scales, as part of the present invention they are extended to the nanostructured regime. This greatly broadens the available classes of materials for which deep, high aspect ratio structures suitable for nanofluidic applications may be fabricated.

Nanostructures that exhibit a gradient in their capacity to transport biomolecular species (through size exclusion or otherwise) may be created by the IL processes discussed herein. Such gradients make separation matrices feasible for highly efficient separation of molecular species. Molecular species may be driven in the direction of the gradient, and thus separated based on their tendency to traverse the gradient, by a variety of driving forces, including, but not limited to, electrophoresis, externally-applied pressure, capillarity, diffusion, and osmosis.

IL represents a convenient method for generating nanostructured separation matrices that contain physical gradients that allow selective transport of chemical species and, thus, may be used to achieve a separation of different chemicals. When compared to other nanolithographic methods of pattern generation (e.g., electron beam lithography, scanning probe lithography), it is more convenient, efficient and inexpensive because it may be used to generate the entire pattern in one, parallel step and is not a serial "writing" technique. Other parallel techniques (e.g., imprint lithography) rely on a primary patterning technique to generate a master that may then be used to produce replicas of nanostructured features in a parallel fashion. While IL is a preferred method to generate nanostructured gradients for molecular separation, a variety of methods could be employed to generate the nanostructured matrix gradient "artificial gels" of the present invention. Gradients in the chemistry of the separation matrix may be prepared by a variety of methods as well, including those based on IL.

The use of IL allows such nanostructured separation matrices to be produced easily and very inexpensively. Nanostructures in which channels are on the order of the excluded size of dissolved biomolecules allow an enhanced flexibility in separation. Higher resolution may be obtained in combination with any of the following mechanisms namely, size exclusion, electrophoretic mobility, isoelectric point, asymmetric diffusion, entropic trapping, hydrophobic interaction and affinity interaction (molecular recognition), as well as others. The gradient matrices produced allow efficient separation and identification of biomolecules such as native proteins and protein complexes in addition to denatured proteins and nucleic acids.

Nanolithography-generated systems have advantages over conventional systems in terms of (1) the virtually perfect uniformity of pore size and pore size distribution from device to device, and (2) the flexibility to precisely define the required distribution (gradient) of pore sizes and pore chemistries. This high degree of reproducibility and versatility in nanofabrication will result in the ability to construct separation devices that exhibit unprecedented degrees of flexibility (resolution, dynamic range) and reproducibility in their separation characteristics.

The separation gradient may be formed by a variety of means including, for example, nanolithography (e.g., IL, electron beam, local probe, nanoimprint) and pattern transfer (etching, deposition, lift-off) means.

Figure 6:
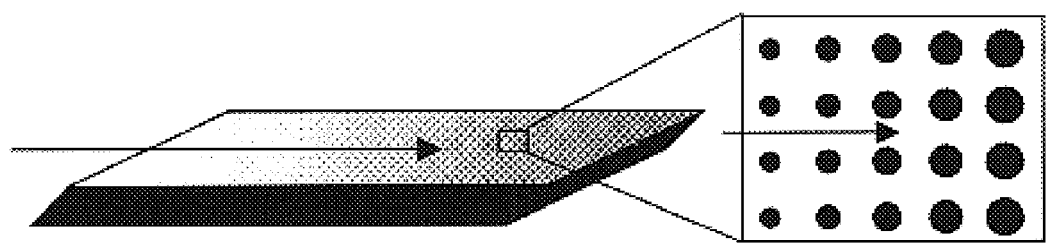
FIG. 6 illustrates in schematic form a nanostructured gradient (chirped) separation matrix.

FIG. 6 shows a schematic of a nanostructured gradient (chirped) separation matrix. The separation gradient may be formed by a variety of means including nanolithography (e.g., IL, electron beam, local probe, nanoimprint) and pattern transfer (etching, deposition, lift-off) means. FIG. 6 illustrates a graded array of nanostructures. The aperture size between the nanostructures approaches molecular dimensions. The arrows signify the direction of movement of molecular species comprising the mixture to be separated and the direction of separation. The height of the nanostructures is preferably sufficiently larger (e.g., 100 nm–1 $\mu$m) than the diameter to allow for higher throughput of the separated species.

Multiple-exposure IL moiré patterns provide for cyclic gradients that may be used for simultaneous manufacture of multiple structures. Gradients may also be fabricated across uniform patterns by non-uniform deposition or etching using properly designed deposition and/or etching tools and techniques such as oblique incidence of etch/deposition atomic/molecular species (shadowing). Analogous techniques may be used in generation of gradients in surface modification chemistry incorporated into the array.

Figure 7A:
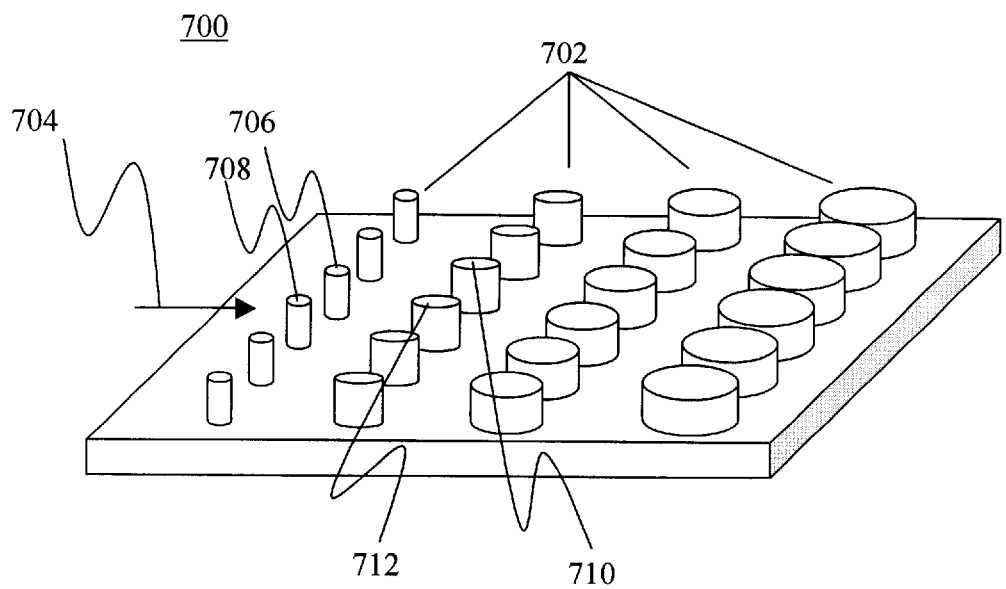
FIGS. 7A and 7B show perspective and top schematic views, respectively, of a nanostructured matrix according to the present invention.
Figure 7B:
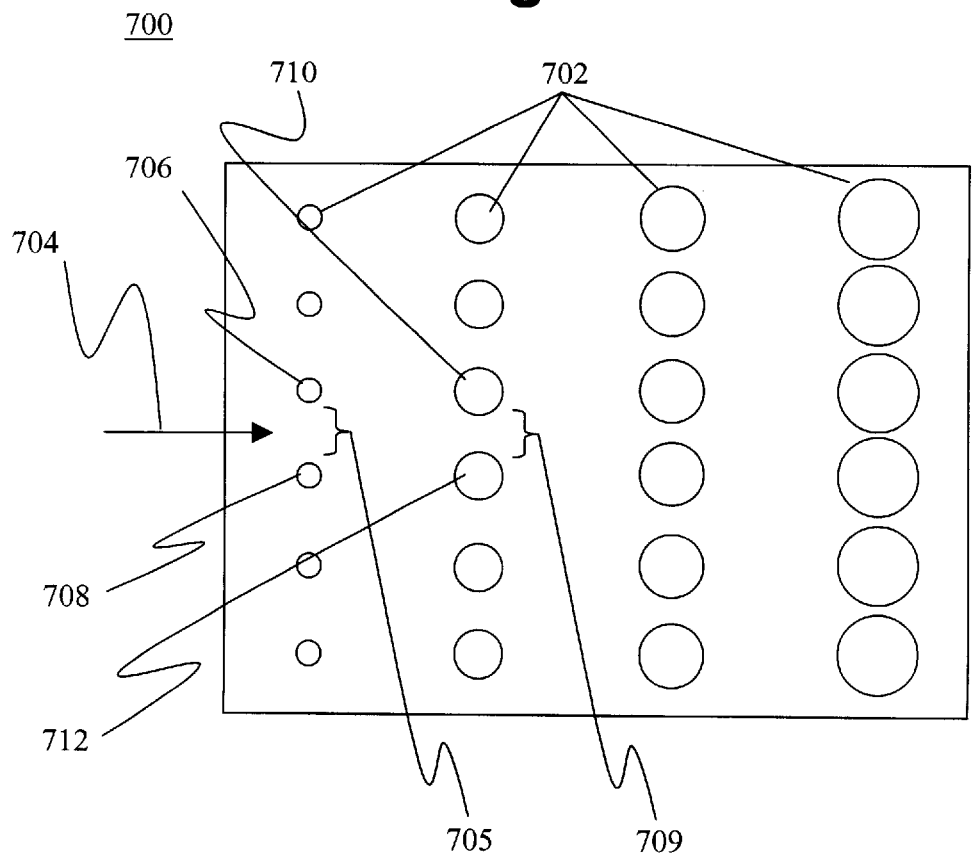

FIGS. 7A and 7B show a perspective view and a top view, respectively, of a nanostructured matrix according to the present invention. Matrix 700 has a plurality of protrusions 702. A sample containing some concentration of molecules moves in the direction of arrow 704. The diameter of channel 705 between protrusion 706 and protrusion 708 is larger than the diameter of channel 709 between protrusions 710 and 712. This change provides a gradient such that larger molecules are inhibited from moving the entire length of matrix 700 once the molecules encounter channels between two protrusions that are smaller than the diameter of the molecule. FIGS. 7A and 7B may be extended to formation of channels to delineate the pathway for molecule movement.

Figure 8A:
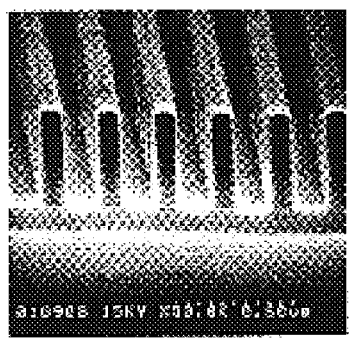
FIGS. 8A, 8B and 8C show high aspect ratio nanostructures fabricated by interferometric lithography and pattern transfer with FIG. 8A showing dense 150 nm photoresist lines, FIG. 8B showing an isolated 50 nm photoresist line, and FIG. 8C showing 50 nm wide walls etched in Si.
Figure 8B:
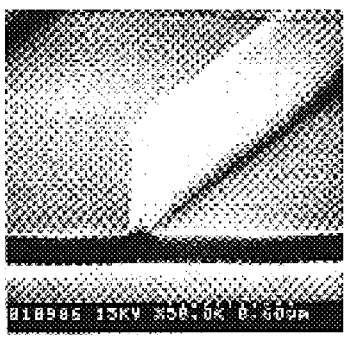
Figure 8C:
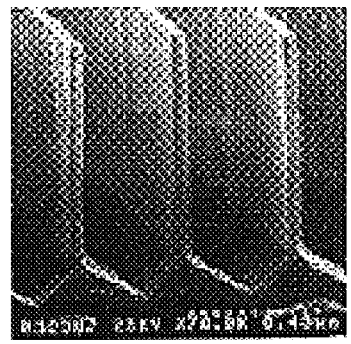

As an example of channel formation according to the present invention, IL and anisotropic wet etching of Si allow the creation of open, parallel nanostructured channels (e.g. uncapped in the direction perpendicular to the surface) with lateral features on the order of biomolecular length scales (~1–10 nm) but with overall dimensions reaching the microscopic (~100 μm) or even macroscopic (~1 cm or greater) scales. Depending upon the dimensions, molecular transport mechanisms may include diffusion, electrophoresis or bulk-flow. The relatively large vertical scale is sufficient to allow high throughput of molecules and external pumping using either electrokinetic or electro-osmotic forces. Examples of high aspect ratio IL nano structured samples are shown in FIGS. 8A, 8B and 8C. Such architectures are applicable to channel and post arrays that are of interest for the separation of proteins and large DNA molecules.

Arrays of nano structures (either of uniform size or with a gradient of sizes) may be surface-modified with chemical species that enhance the separation characteristics of the matrix. These chemical species may be distributed uniformly over the nanostructured separation matrix or may be distributed in a gradient (continuous or discrete) in the direction of separation over the matrix. These chemical species may include small organic molecules, polymers, receptors or other biomolecules.

IL may be used to expose patterns on photoresist on silicon or other materials (which are later etched).Silicon and some other materials may have an oxide surface that is easily modified with silanization reagents. Synthetic strategies for modification are also available for other materials (besides oxides), including native silicon and noble metals (e.g., gold). Monomolecular layers may be created from a wide range of commercially- or synthetically-available chemical species that will enhance separation characteristics based on the type and degree of interaction of chemical species being separated with the walls of the surface-modified nanostructured separation matrix. Examples of types of surface modifications (either as gradients or uniform) include the use of hydrophilic oligomeric and polymeric species e.g., poly-ethylene glycol (PEG) to minimize interactions of chemical species especially proteins, with nanostructured surfaces; use of hydrophobic molecular or oligomeric species to elicit hydrophobic interaction of chemical species (esp. proteins) with nanostructured surfaces; use of mixtures of hydrophobic and hydrophilic species (polar, apolar, H-bonding, ionic) to tune interaction of different chemical species with surfaces; use of ionic molecular species and mixtures of ionic species to tune interaction of different chemical species with surfaces; use of biomolecular or organic receptors to elicit molecular recognition of small molecules, polymers, proteins, DNA, RNA, or oligonucleotides with the surface; use of oligonucleotide probes to tune interactions of DNA, RNA or nucleic-acid binding proteins with the surface; use of cyclodextrins, macrocyclic antibiotics, crown ethers and other chiral selectors to tune enantiomeric interactions of chemical species with the surface; and use of stimuli-responsive (smart) molecules or polymers to allow external control of interaction of chemical species with the nanostructured surface.

Figure 9:
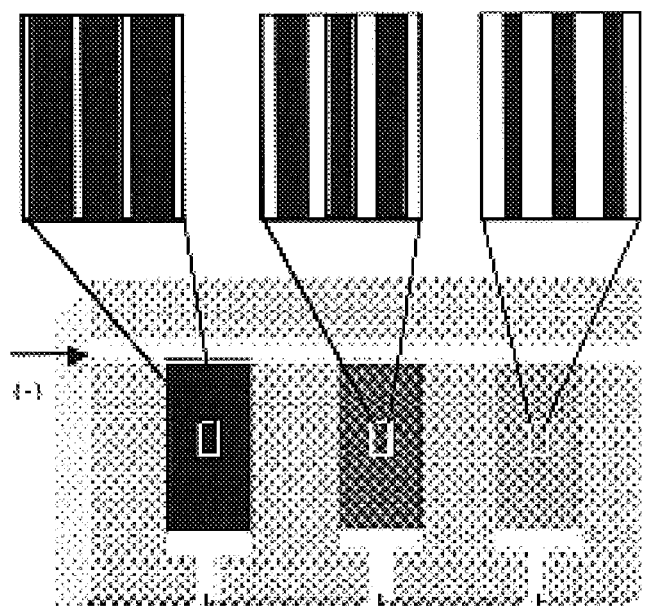
FIG. 9 is a schematic of a purification chip containing several biomolecular sieves with different aperture sizes.

Other types of separation systems of the present invention may be thought of as having discontinuous gradients. These separation systems contain areas with different aperture sizes, and may be made either by separate exposures at different intensity, at different pitches through shadow masks, or by using multiple exposure techniques to eliminate rows and/or columns of pillars. Such systems are especially useful in that they will allow recovery of separated compounds (purification). An example of a schematic of such a design is presented in FIG. 9. A mixture of negatively charged biomolecules (e.g., SDS treated proteins or DNA) is loaded at the left, top corner of the chip, and is driven electrophoretically across a series of discrete "sieves" that have increasing aperture size, such that smaller, and then larger molecules pass through the consecutive sieves. Each sieve is connected to a separate outlet port, such that different sized biomolecules may be collected at different outlets. If necessary, these attachments may be made through the top or bottom of the chip, and additional separation in this direction may then be combined with recovery. More sophisticated designs allow continuous purification and sample recycle.

Microfabricated Integrated Multi-Dimensional, Multi-Technique Separation Systems The present invention allows a variety of different separation strategies (electrophoresis, iso-electric focusing, affinity chromatography, hydrophobic interaction chromatography, enantiomeric resolution) to be used on a single monolithic device, thus allowing for ease of use and compactness of instrumentation.

The closest existing commonly used multi-technique separation is two-dimensional gel electrophoresis (2DGE). In traditional 2DGE, proteins are first separated according to isoelectric point, followed by resolution by mass-to-charge-ratio using standard polyacrylamide electrophoresis. This process requires that two separate electrophoretic procedures be performed, each requiring manipulation of the sample. A nanostructured matrix of the present invention allows for sequential analysis on a single chip, thus reducing sample loss and diffusion. The wide range of chemical modifications and array architecture allowed by IL devices will also permit separation of proteins by means in addition to size and isoelectric point, either by appropriate chemical patterning and valving of the device, or by addition of a third separation and/or dilution dimension.

In some cases, the open nanostructured channels may be sealed in order to provide closed ducts, through which solutions may diffuse or be pumped. This may be done by bonding a "roof" to the wafer containing the open nanostructured channels to form closed channels. There are several methods available (currently in use for microscale devices) that may be explored. One alternative is a bonding procedure that uses sodium silicate (deposited through spin-coating) as an adhesive, which may be cured at room temperature overnight. This method used on glass substrates results in mechanical strengths comparable to high temperature bonding techniques.

A second alternative is to use a molecular bonding process. Silane monolayers would be formed on both the tops of the protrusions on the nanostructured channel wafer (e.g., through contact printing) and the polished "roof" of the channels. The silane molecules used to form the monolayers would be terminated with complementary functional groups (e.g., amines and aldehydes) such that the two silane monolayers would chemically bond. This would result in almost a single monolayer between the two surfaces, and prevent clogging of the nanostructured channels. Since this technique requires no heat and may be done in aqueous media, delicate proteins or other molecules would not be damaged during the bonding process. Finally, a "roof" may be held in place by capillary forces alone. Such a scheme may work well where low pressures flows are involved (diffusive separations, electrophoresis or electro-osmosis), but it may not be suitable for externally pumped flows.

Fabrication of separation matrices systems from materials (e.g., Si and quartz) commonly used in the fabrication of integrated circuits is advantageous. They have unique etching and surface modification characteristics that are well established, and may be easily implemented in existing microfabrication facilities for the development of complex separation and detection systems. Other materials with advantageous characteristics may also be used.

The nanostructured matrix of the present invention may be used for two-dimensional gel electrophoresis, and a number of other separation techniques may be combined with size exclusion and/or isoelectric focussing, In addition, the matrix has the capability of expansion beyond two dimensions.

The analytical potential of a nanostructured matrix of the present invention may be enhanced by combining two or more standard types of analysis on a single platform. Among the possible combinations of separation technologies applicable to this platform are those analogous to PAGE, isoelectric focusing, hydrophobic interaction chromatography, affinity chromatography, enantiomeric resolution and capillary electrophoresis. The matrix lends itself well in carrying out equivalent molecular weight separations, with either electrical currents or flow as the driving force.

Figure 10A:
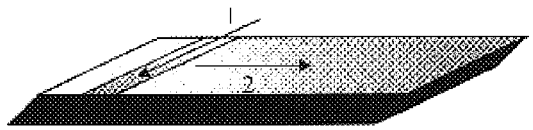
FIGS. 10A and 10B are schematics depicting monolithic multi-technique separation systems according to the present invention with FIG. 10A showing a 2-technique, (2-dimensional) separation in a single level separation system and FIG. 10B showing an exploded view of a 2-technique separation in a two-level separation system.
Figure 10B:
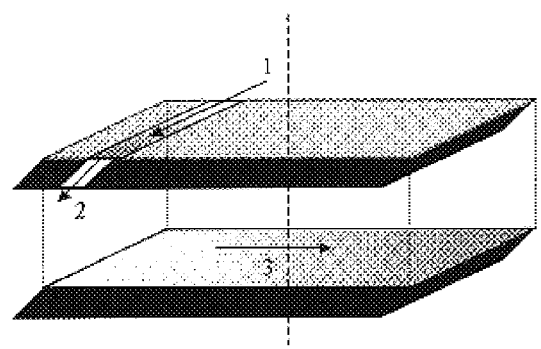

FIGS. 10A and 10B schematically depict a model separation system according to the present invention. Multi-technique separations may be performed either in the plane of a particular separation matrix (FIG. 10A) or may be performed in a multi-level structure (FIG. 10B). In FIG. 10A, molecules are separated along arrow 1 and then along arrow 2. The separation matrices corresponding to arrows 1 and 2 may be any of the types described herein. The driving force for transport along the direction of the arrows may be any of those described herein. FIG. 10B shows an exploded view of a two-technique separation in a two-level separation system. The complexity of the systems and the number of separation stages or techniques may be increased or modified as needed.

FIG. 10B exemplifies the combination of two or more gels (with or without gradients) in a multi-level, multi-stage device that allows for combinations of different separation strategies (e.g. electrophoresis, isolectric focusing (IEF), affinity chromatography, hydrophobic interaction chromatography) on a single monolithic device. For example, IEF and size exclusion may be used in a manner similar to 2DGE. These two dimensions, however, may also be combined with another dimension, for example, antibody affinity chromatography, to achieve more precise separations. The types of separations themselves may be combined in a nearly infinite variety of combinations to achieve the best possible separations for the molecules. In addition, this system allows for sequential analysis on a single chip, thus increasing efficiency of sample use.

The present invention is useful in proteomics by enabling combinations of different types of analysis on a single chip, e.g. size exclusion in one dimension with chemical differentiation in the second. A third dimension, oriented perpendicular to the two dimensional array on the chip, may then be used for further separation, or for recovery and further characterization of isolated spots.

The present invention will also find use in protein separations for forensic and medical diagnostic tools and in the separation of bioengineered proteins. Forensic analysis and diagnostics, for example, depend heavily upon differentiation between carbohydrate moieties on blood proteins and bacterial cells. Discovery of clinically useful drugs often depends on identifying interactions with specific cellular receptors, which are usually glycoproteins. Capillary electrophoresis has been extremely useful in separations of acid carbohydrates, with derivatization of the column. The present invention allows for the separation of two properties, for example glycoprotein size and carbohydrate content on a single platform, thus eliminating the need for cumbersome recovery between steps and increasing the yield of useful analyte.

Recently, techniques utilizing antibody-based affinity separations have transitioned from clinical laboratories to those for environmental monitoring. The present invention allows sequential analysis of at least two different properties, thus increasing sensitivity of analysis, with particular interest for environmental monitoring.

The present invention allows for separation of a variety of sizes of nucleic acid species, and thus, may be used for separations that are currently done by standard and pulsed-field gel electrophoresis, as well as nucleic acid sequencing. In addition, modification of the device by nucleic acid-binding molecules (e.g. proteins, drugs) allows for isolation of relevant target sequences from previously uncharacterized genomes, or for isolation of the biocomplex formed with the nucleic acid. Because separation may be multidimensional, these devices may be attached in series with a reaction chamber (for example, a PCR thermocycler) and the resultant product directly fed into the separation platform for purification and analysis in a single device.

IL may be used to create nanostructures on a variety of substrates. IL, in combination with other standard lithographic and microfabrication methodologies, may be used to create a variety of nanostructures which may be modified in many ways to produce tools for separation of relevant biomolecules. These have advantages over contemporary molecular separation systems because they exhibit superior performance (resolution, sensitivity, dynamic range, applicability, reproducibility), may be parallel-produced at relatively low cost, and are extremely flexible in terms of chemical modifications. They have defined features that may be reproducibly made, enable flexible and complex separation, and may be used with existing bioseparation and detection strategies.

EXAMPLES

Example 1

Figure 11:
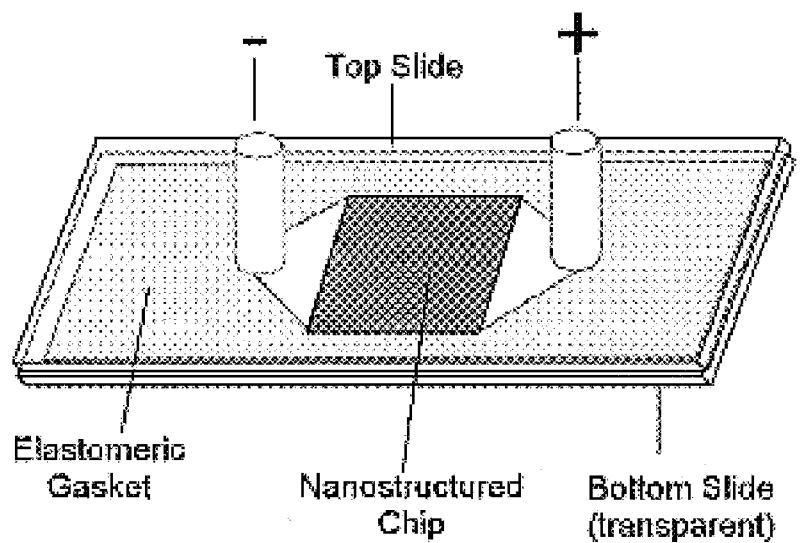
FIG. 11 is a schematic of a simple electrophoretic cell that incorporates a nanofluidic separation matrix patterned using IL.

Design and construction of microscale electrophoresis cells incorporated much of the characteristics of the present invention into a compact system. The cell preferably has the following characteristics: (1) electrochemical current and fluid flow must be restricted to occur only through the separation matrix; (2) loading and stacking functions must be included; (3) monitoring of mobility and biomolecular detection must be possible (e.g., through fluorescence imaging); and (4) for certain applications, separated compounds must be recoverable. Simple methods have been used for incorporating nanostructured silicon/silica chips into electrophoresis cells that satisfy criteria (1–3) above. For example, simple methods of rapid prototyping of elastomeric gasket materials have been used. FIG. 11 presents a schematic of a simple electrophoresis cell design. The cell design allows formation of a electrophoretic nanofluidic system that incorporates a nanopatterned oxidized silicon chip of arbitrary dimension and arbitrary nanofluidic design. Thus, the feasibility of use of chips with nanostructured surface features that have been prepared using IL has been established. Using such a simple cell, the experiments have demonstrated that electrophoretic mobility may be used to transport proteins through nanostructures formed through IL lithographic patterning of silicon wafers. Protein loading was achieved through tubing attached to the electrophoresis cell. Uniform stacking of the proteins against the nanostructured chip may be achieved through optimization of the geometry of the loading tube with respect to the chip. Gas bubbles that evolve at the electrode surfaces may be restricted from entering the separation matrix by a hydrogel membrane.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A matrix comprising an array of nanostructures arranged on a substrate, wherein said array has a continuous gradient property across the plane of said substrate.

2. The matrix of claim 1, wherein said nanostructures comprise channels.

3. The matrix of claim 2, wherein said channels are closed.

4. The matrix of claim 2, wherein said nanostructures further comprise protrusions.

5. The matrix of claim 1, wherein said nanostructures comprise protrusions.

6. The matrix of claim 1, wherein said substrate comprises Si.

7. The matrix of claim 1, wherein said matrix comprises a semiconductor chip.

8. The matrix of claim 1, wherein said matrix comprises a biochip.

9. A method for forming an array comprising the steps of:
(a) providing a substrate; and
(b) forming nanostructures on said substrate to form an array, wherein said array has a continuous gradient property across the plane of said substrate.

10. The method of claim 9, wherein step (b) comprises etching.

11. The method of claim 9, wherein said nanostructures comprise channels.

12. The method of claim 9, wherein step (b) comprises etching nanostructures using interferometric lithography.

13. The method of claim 12, wherein said nanostructures comprise channels.

14. A separation method comprising the steps of:
(a) providing a matrix comprising an array of nanostructures arranged on a substrate, wherein said array has a continuous gradient property across the plane of said substrate; and
(b) conducting at least one biomolecule separation process to separate biomolecules in a composition containing a plurality of biomolecules using said matrix.

15. The method of claim 14, wherein said at least one biomolecule separation process comprises at least two biomolecule separation processes.

16. The method of claim 15, wherein each of said two biomolecule separation process are conducted at right angles to each other.

17. The method of claim 15, further comprising conducting a third biomolecule separation process on biomolecules separated by said at least two biomolecule separation processes.

18. The method of claim 15, wherein one of said at least two biomolecule separation processes comprises a size exclusion separation process.

19. The method of claim 18, wherein one of said at least two biomolecule separation processes comprises a mass to charge gel electrophoretic mobility separation process.

20. The method of claim 18, wherein one of said at least two biomolecule separation processes comprises an isoelectric focusing separation process.

21. The method of claim 18, wherein one of said at least two biomolecule separation processes comprises an asymmetric diffusion separation process.

22. The method of claim 18, wherein one of said at least two biomolecule separation processes comprises an entropic trapping separation process.

23. The method of claim 18, wherein one of said at least two biomolecule separation processes comprises a hydrophobic interaction chromatography separation process.

24. The method of claim 18, wherein one of said at least two biomolecule separation processes comprises an affinity chromatography separation process.

25. The method of claim 18, wherein one of said at least two biomolecule separation processes comprises an enantiomeric resolution separation process.

26. The method of claim 18, wherein one of said at least two biomolecule separation processes comprises a capillary electrophoresis separation process.

27. The method of claim 14, wherein said at least one biomolecule separation process comprises a size exclusion separation process.

28. The method of claim 14, wherein said nanostructures comprise channels.

29. The method of claim 28, wherein said channels are closed.

30. The method of claim 28, wherein said nanostructures further comprise protrusions.

31. The method of claim 14, wherein said nanostructures comprise protrusions.

32. The method of claim 14, wherein said substrate comprises Si.

33. The method of claim 14, wherein said matrix comprises a semiconductor chip.

34. The method of claim 14, wherein said matrix comprises a biochip.

* * * * *